United States Patent [19]

Lee et al.

[11] Patent Number: 4,859,781

[45] Date of Patent: Aug. 22, 1989

[54] RECOVERY OF N-METHYL-2-PYRROLIDONE

[75] Inventors: Fu M. Lee; Joseph G. Ceurvorst, both of Bartlesville, Okla.

[73] Assignee: Phillips Petroleum Company, Bartlesville, Okla.

[21] Appl. No.: 319,015

[22] Filed: Mar. 3, 1989

[51] Int. Cl.$^4$ ................ C07D 201/16; C07D 207/267
[52] U.S. Cl. .................................................. 548/555
[58] Field of Search ........................................ 548/555

[56] References Cited

U.S. PATENT DOCUMENTS 3,290,329 12/1966 Doerfel ................................ 548/555
3,687,907 8/1972 Crouch et al. ...................... 260/79.1
3,697,487 10/1972 Cines .................................. 260/79.1
4,501,902 2/1985 Clearly ............................... 548/555

FOREIGN PATENT DOCUMENTS 0259889 12/1969 U.S.S.R. .

Primary Examiner—David B. Springer
Attorney, Agent, or Firm—K. K. Brandes

[57] ABSTRACT

In a process for recovery N-methyl-2-pyrrolidone from a liquid aqueous medium (preferably a brine) by liquid-liquid extraction, the improvement comprises using a branched aliphatic C5-C7 alcohol as extractant. In a particular embodiment, the liquid aqueous medium is an effluent from a poly(arylene sulfide) process.

17 Claims, No Drawings

RECOVERY OF N-METHYL-2-PYRROLIDONE

BACKGROUND OF THE INVENTION

In one aspect, this invention relates to the extraction of N-methyl-2-pyrrolidone (NMP) from an aqueous medium. In another aspect, this invention relates to the recovery of NMP from an effluent of a process for preparing poly(arylene) sulfide.

The extraction of N-methyl-2-pyrrolidone (NMP) from aqueous solutions and/or slurries with polar organic solvents is known, and has been described in U.S. Pat. Nos. 3,687,907 and 3,697,487. Of particular importance is the extraction of NMP from effluents of a process for making poly(arylene sulfide), in particular poly(phenylene sulfide), also referred to as PPS. PPS process effluents generally are aqueous brines which comprise NaCl, NMP and other organic and inorganic compounds, as has been disclosed in the above-cited patents. A linear aliphatic alcohol, 1-hexanol, has been used as a extractant for NMP, as is disclosed in U.S. Pat. No. 3,687,907. However, there is an ever present need to discover more effective extractants for NMP than 1-hexanol.

SUMMARY OF THE INVENTION

It is an object of this invention to recover NMP from an aqueous medium by liquid-liquid extraction. It it another object of this invention to extract NMP from an effluent of a process for preparing poly(arylene sulfide). It is a further object of this invention to use an aliphatic alcohol as extractant for NMP. Other objects and aspects of this invention will be apparent from the detailed description and the appended claims.

In accordance with this invention, in a process for recovering N-methyl-2-pyrrolidone (NMP) from a liquid aqueous medium comprising liquid-liquid extraction with an organic extractant, the improvement comprises employing at least one branched aliphatic alcohol having 5-7 carbon atoms per molecule as extractant.

In one preferred embodiment, the extractant is 2-ethyl-1-butanol or 2-methyl-1-pentanol or a mixture thereof. In another preferred embodiment, the substantially liquid aqueous medium contains dissolved alkali metal halide and dispersed poly(arylene sulfide) particles. In a further preferred embodiment, the substantially liquid aqueous medium is an effluent from a process of preparing poly(arylene sulfide) by reaction of at least one polyhalo-substituted aromatic compound (in particular 1.4-dichlorobenzene) with an alkali metal hydrogen sulfide (in particular NaHS) in the presence of NMP.

DETAILED DESCRIPTION OF THE INVENTION

The extraction of NMP from an aquoeus medium with the extracting of this invention can be carried out in any suitable manner, substantially in accordance with the procedures described in U.S. Pat. Nos. 3,687,907 and 3,697,487, the disclosures of whichare herein incorporated by reference. Liquid-liquid extraction techniques are well known to those having ordinary skill in the art, and are not described in detail herein. Surveys of such liquid-liquid extraction techniques are provided in Kirk-Othmer Encyclopedia of Chemical Technology, Third Edition, Volume 9, 1980, John Wiley and Sons, Inc., pages 672-716; and in an article entitled "The Essentials of Extraction" by Jimmy L. Humphrey et al, Chemical Engineering, Sept. 27, 1984, pages 76 and 84-88.

In preferred embodiments of this invention, the NMP-containing aqueous medium is a brine and contains at least one dissolved alkali metal halide, in particular alkali metal chloride (more preferably NaCl), which can be present in any suitable concentration (e.g., 0.1-20 weight-%), preferably about 1-115 weight-% alkali metal halide. The aqueous medium can contain water at any suitable concentration, preferably about 20 to about 95 weight-% $H_2O$. The aqueous medium can contain NMP at any suitable concentration, preferably about 2 to about 50, more preferably about 5 to about 40, weight-% NMP. The aqueous medium can contain other impurities, such as 1,4-dichlorobenzene, NaSH, $Na_2S$, sodium acetate, and dispersed poly(phenylene) sulfide PPS particles, as has been described in the above-cited patent references.

The extraction process can be carried out at any suitable temperature (preferably at about 20° to about 100° C.), at any suitable pressure (preferably at about 1-20 atm., more preferably at about 1 atm.), and at any suitable weight ratio of alcohol extractant to NMP-containing aqueous medium (preferably at about 0.5:1 to about 2:1).

The extractant, which exhibits little solubility in water, can be any branched aliphatic alcohol having 5-7 carbon atoms per molecule, such as 2-methyl-1-butanol, 3-methyl-1-butanol, 3-methyl-2-butanol, 2-methyl-1-pentanol, 3-methyl-1-pentanol, 2-ethyl-1-butanol, 3-methyl-2-pentanol, 3-ethyl-1-pentanol, 2-methyl-1-hexanol, 3-methyl-1-hexanol, 4-methyl-1-hexanol, 4-methyl-2-hexanol, and the like, and mixtures thereof; preferably 2-ethyl-1-butanol or 2-methyl-1-pentanol.

After the extraction step, i.e., the step of intimately contacting (preferably with agitation) the aqueous medium with the extractant, two liquid phases (i.e., an aqueous raffinate phase from which at least a portion of the NMP has been removed, and a branched alcohol containing extract phase which contains the portion of NMP which has been removed from the aqueous medium) are formed. The two liquid phases are then separated from one another. This can be achieved by any suitable means, such as draining of the lower phase or of the upper phase or of both phases, or by any other conventional separation technique.

The subsequent separation of the alcohol extractant from NMP (both contained in the extract phase) can be achieved by any suitable means, such as fractional distillation. The alcohol can be recycled for reuse in the extraction step, and NMP can be recycled to the process from which the aqueous NMP-containing medium originated, e.g., to a poly(arylene sulfide) reactor.

The following example is presented to further illustrate the invention and is not to be construed as unduly limiting the scope of this invention.

EXAMPLE

An aqueous feed comprising water, NMP and NaCl was contacted with alcoholic extractants in a one-stage liquid-liquid glass extractor (capacity: about 300 cc; equipped with inside stirrer, internal heating means, thermometer and condenser) at about 80° C. and an extractant: feed weight ratio of about 0.9:1. After the feed and the extractant had been intimately contacted in the extractor, the two liquid phases which formed were allowed to separate and were then analyzed. Results of these tests are summarized in Table I.

TABLE I

| Extractant | Feed (g) + Extractant (g) | | Bottom Phase (g) | Top Phase (g) | NMP Recovery (Wt %)[1] | Extractant Recovery (Wt %)[2] |
|---|---|---|---|---|---|---|
| 2-Ethyl-1-butanol | H2O | 40.24 | 33.59 | 5.91 | | |
| | NMP | 13.89 | 3.86 | 10.64 | 72.2 | 99.2 |
| | NaCl | 1.45 | 1.44 | 0.00 | | |
| | Extr. | 50.00 | 0.42 | 48.34 | | |
| 2-Methyl-1-pentanol | H2O | 54.32 | 48.27 | 7.64 | | |
| | NMP | 18.76 | 6.05 | 11.59 | 67.8 | 99.0 |
| | NaCl | 1.95 | 1.95 | 0.00 | | |
| | Extr. | 67.60 | 0.66 | 64.76 | | |
| 1-Hexanol | H2O | 54.32 | 46.42 | 9.42 | | |
| | NMP | 18.76 | 6.39 | 12.28 | 65.9 | 99.4 |
| | NaCl | 1.95 | 1.95 | 0.00 | | |
| | Extr. | 67.60 | 0.43 | 64.75 | | |

[1]NMP Recovery = (NMP in Feed − NMP in Bottom Phase) ÷ (NMP in Feed) × 100
[2]Extractant Recovery = (Extractant in Feed − Extractant in Bottom Phase) ÷ (Extractant in Feed) × 100

Test results in Table I clearly show the greater effectiveness as NMP extractants of the two branched hexanols versus linear 1-hexanol.

Additional tests revealed that the NMP recovery by liquid-liquid extraction was greater at a higher NaCl concentration of the feed (up to 15 weight-% NaCl).

Reasonable variations and modifications, which will be apparent to those having ordinary skills in the art, can be made in this invention without departing from the spirit and scope thereof.

That which is claimed is:

1. In a process for recovery N-methyl-2-pyrrolidone from a liquid aqueous medium comprising the step of liquid-liquid extraction with an organic extractant, the improvement which comprises employing a branched alkyl alcohol having 5–7 carbon atoms per molecule as extractant.

2. A process in accordance with claim 1 wherein said alcohol has 6 carbon atoms per molecule.

3. A process in accordance with claim 1 wherein said alcohol is 2-ethyl-1-butanol.

4. A process in accordance with claim 1 wherein said alcohol is 2-methyl-1-pentanol.

5. A process in accordance with claim 1 wherein said liquid aqueous medium comprises at least one alkali metal halide.

6. A process in accordance with claim 1 wherein said liquid aqueous medium comprises NaCl.

7. A process in accordance with claim 6 wherein the NaCl concentration in said liquid aqueous medium is about 1–15 weight-% NaCl.

8. A process in accordance with claim 1 wherein said liquid aqueous medium is an effluent from a process for preparing poly(arylene sulfide) by reaction of at least one polyhalo-substituted aromatic compound with an alkali metal hydrogen sulfide in the presence of N-methyl-2-pyrrolidone.

9. A process in accordance with claim 1 wherein the concentration of N-methyl-2-pyrrolidone in said liquid aqueous medium is about 2–50 weight-%.

10. A process in accordance with claim 1 wherein said liquid-liquid extraction is carried out at a temperature of about 20°–100° C.

11. A process in accordance with claim 1 wherein said liquid-liquid extraction is carried out at a weight ratio of said extractant to said liquid aqueous medium in the range of from about 0.5:1 to about 2:1.

12. A process in accordance with claim 11 wherein said extractant is 2-ethyl-1-butanol.

13. A process in accordance with claim 12 wherein said feed contains about 1–15 weight-% NaCl.

14. A process in accordance with claim 11 wherein said extractant is 2-methyl-pentanol.

15. A process in accordance with claim 14 wherein said feed contains 1–15 weight-% NaCl.

16. A process in accordance with claim 1 comprising the additional steps of forming an aqueous raffinate phase from which at least a portion of N-methyl-2-pyrrolidone has been removed and an extract phase which contains said extractant and N-methyl-2-pyrrolidone having been removed from said liquid aqueous medium, and thereafter separating said raffinate phase from said extract phase.

17. A process in accordance with claim 1 comprising the additional steps of separating said extractant from N-methyl-2-pyrrolidone contained in said extract phase, and recovering said extractant and said N-methyl-2-pyrrolidone.

* * * * *